(12) United States Patent
Kang et al.

(10) Patent No.: US 6,920,197 B2
(45) Date of Patent: Jul. 19, 2005

(54) VEHICLE-CARRIED MOBILE CONTAINER INSPECTION APPARATUS

(75) Inventors: Kejun Kang, Beijing (CN); Wenhuan Gao, Beijing (CN); Yinong Liu, Beijing (CN); Yuanjing Li, Beijing (CN); Jianmin Li, Beijing (CN); Chuanxiang Tang, Beijing (CN); Junli Li, Beijing (CN); Hua Peng, Beijing (CN); Quanwei Song, Beijing (CN); Shuxiong Cao, Beijing (CN); Liwei Song, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 86 days.

(21) Appl. No.: 10/684,492

(22) Filed: Oct. 15, 2003

(65) Prior Publication Data

US 2004/0125914 A1 Jul. 1, 2004

(30) Foreign Application Priority Data

Oct. 16, 2002 (CN) .......................................... 02146208 A

(51) Int. Cl.$^7$ .............................................. G01N 23/04
(52) U.S. Cl. ........................................ 378/57; 378/198
(58) Field of Search .................................... 378/57, 198

(56) References Cited

U.S. PATENT DOCUMENTS

| | | | | |
|---|---|---|---|---|
| 5,692,028 A | * | 11/1997 | Geus et al. | .................... 378/57 |
| 6,058,158 A | * | 5/2000 | Eiler | .......................... 378/57 |
| 6,763,635 B1 | * | 7/2004 | Lowman | ....................... 378/57 |

FOREIGN PATENT DOCUMENTS

| | | |
|---|---|---|
| CN | 1295247 A | 5/2001 |
| CN | 2572400 Y | 9/2003 |
| DE | 40 23 413 A1 | 2/1991 |
| WO | WO 98/00681 | 1/1998 |

\* cited by examiner

*Primary Examiner*—Craig E. Church
*Assistant Examiner*—Thomas R. Artman
(74) *Attorney, Agent, or Firm*—Foley & Lardner LLP

(57) ABSTRACT

A vehicle-carried mobile container inspection apparatus characterized in that the mobile container inspection apparatus comprises a first box-shaped cabin arranged in the front portion of the chassis and provided with a workroom accommodating a scan control module, an image acquisition module and an operation/inspection module; and a second box-shaped cabin and a third box-shaped cabin both arranged on the rear portion of the rotatable platform, in which the second box-shaped cabin is arranged on the top of the third box-shaped cabin, the control unit of the radiation source is accommodated in the second box-shaped cabin, the third box-shaped cabin is arranged under the rotatable platform, the radiation source is arranged in the third box-shaped cabin, the level of the radiation source from which the X-ray beam emit is arranged below the level of the chassis, the scanning vehicle is provided with a driving means to smoothly move the scanning vehicle the rotatable platform is provided with a rotatably driving means, when inspecting a container, the rotatable platform is driven to turn 90 degrees, and the second arm turns into its vertical gesture, so that a portal-shaped frame is formed by means of the parallelogrammical bracket, the first arm and the second arm. The mobile inspection container apparatus is capable of inspecting as broad area as to reach the vehicle chassis. The apparatus comprises two vehicles, in which usually the both vehicles are used, while only one vehicle is used for fulfilling the inspection work in emergency.

4 Claims, 3 Drawing Sheets

VEHICLE-CARRIED MOBILE CONTAINER INSPECTION APPARATUS

FIELD OF THE INVENTION

The present invention relates to a container inspection apparatus, and more particularly relates to a vehicle-carried mobile container inspection apparatus.

PRIOR ART

In the prior art, there have been proposed a kind of trail-type container inspection system since 1990, such as those manufactured by Heimann Systems GmbH and British Aerospace PLC. This kind of system is installed in a fixed site, and a stationary radiation source for generating a high-energy X-ray and an array of detectors for receiving the X-ray penetrating through the container being inspected are both arranged into an inspection passage with shielding walls. A special conveying device is employed so as to move the container to pass through the inspecting passage. During moving the container to pass through the inspection passage, the detectors receive the X-rays penetrating through the container, then the density distribution of the objects in the container is obtained according to signal intensity variations. Then, by transforming the data on the signal intensity to the data on the image gray levels, the radiographic image of the goods contained in the container can be obtained. However, this known inspection system has the following disadvantages: besides the too long inspection passage (at least 60 m), an extra length for a container being inspected to be driven in and out from the two ends of the inspection passage is at least 40 m long, and a set of huge and heavy pulling device is needed. The area of the constructed site is as large as a football-court. Once installed after a long construction period, the system has to be permanently located in the constructed site. So it has such disadvantages as high costs of construction, and inconveniences of maintenance. And it can not be moved or conveyed to the other site for fulfilling the inspection work on demands. In order to overcome these drawbacks, various kinds of vehicle-carried mobile inspection systems have been developed. In the mobile inspection system proposed by Heimann Systems GmbH, all the equipments such as the radiation source, the detectors and the control units are mounted on a vehicle with a trailer chassis, and a workroom is arranged in the rear part of the chassis. However, there are many problems in this kind of mobile inspection system resulted from the vehicle's structure itself. For example, the manufacturing process for the vehicle is complicated, the vehicle has a great bulk with its weight over 40 tons. Moreover, in this kind of the mobile inspection system, the operators have to work for a long time in the workroom together with its instruments. That is to say, the operators have to work in an adverse and narrow working space in which it is of certain hazardous radiation.

The Chinese Patent ZL99253458.5 discloses a double vehicle carried mobile container inspection apparatus with accelerator as its radiation source, in which two vehicles are used to carry the entire apparatus. Although the operators work in one vehicle so as to have a comfortable working environment, while the main inspection instruments stay in the other vehicle, the inspection apparatus cannot inspect as broad area as to reach the vehicle chassis. So the scope of inspection is much limited. Moreover, as no diesel generator is arranged on the scanning vehicle, the inspection apparatus cannot be used in every possible cases, and the two vehicles must be used together. As a result, it is more difficult to layout the inspection apparatus in any emergency situation.

SUMMARY OF THE PRESENT INVENTION

The object of the present invention is to provide a mobile inspection container apparatus which is capable of inspection as broad as to beneath the vehicle chassis. The apparatus comprises two vehicles. Usually the both vehicles are used, while only one vehicle is used for fulfilling the inspection work in emergency situation.

According to one aspect of the present invention, there is provided a vehicle-carried mobile container inspection apparatus comprising a rotatable platform arranged in the rear portion of the chassis of the scanning vehicle, a parallelogrammical bracket arranged on the rotatable platform, formed by four linkage bars hinged one to another and driven by an uprighting means, a first arm extended from the upper horizontal bar of the parallelogrammical bracket and provided with detectors, and a second arm, the upper end of which is associated with the first arm at the end of the first arm opposite to the parallelogrammical bracket, and a second arm is also provided with detectors, characterized in that the mobile container inspection apparatus further comprises a first box-shaped cabin arranged in the front portion of the chassis and provided with a workroom accommodating a scan control module, an image acquisition module and an operation/inspection module; and a second box-shaped cabin and a third box-shaped cabin both arranged on the rear portion of the rotatable platform, in which the second box-shaped cabin is arranged on the top of the third box-shaped cabin, the control unit of the radiation source is accommodated in the second box-shaped cabin, the third box-shaped cabin is arranged under the rotatable platform, the radiation source is arranged in the third box-shaped cabin, the level of the radiation source from which the X-ray beam emit is arranged below the level of the chassis, the scanning vehicle is provided with a driving means to smoothly move the scanning vehicle; the rotatable platform is provided with a rotatably driving means, when inspecting a container, the rotatable platform is driven to turn 90 degrees, and the second arm turns into its vertical gesture, so that a portal-shaped frame is formed by means of the parallelogrammical bracket, the first arm and the second arm, a fan-shaped X-ray section is formed after the rear end of the chassis and in the plane where the first arm and the second arm are in operation.

Preferably, the first box-shaped cabin is further provided with a diesel generator with its control units.

Preferably, the apparatus further comprises a control vehicle accommodating an image acquisition module, an operation/inspection module, and a diesel generator with its control unit.

Preferably, the chassis is the same as that used in a common vehicle.

According to the present invention, the mobile container inspection apparatus comprises a control vehicle accommodating the operation control and image processing units, and a scanning vehicle for accommodating the every necessary instruments for inspecting a container. There are arranged three box-shaped cabins in the scanning vehicle. In the first cabin, there is arranged a diesel generator for ensuring inspection apparatus to work at any situations, i.e., even if the public power supply is broken off or not available at all, the scanning vehicle can work independently to fulfill the normal container inspection.

Further, according to the present invention, there is a workroom not only in the control vehicle but also in the first cabin of the scanning vehicle. Therefore, wherever the apparatus according to the present invention is located to perform the container inspection, the operators can always work in a desired enough environment.

Further, according to the present invention, the radiation source is arranged under the rotatable platform, lowing the level of the radiation source. By properly adjusting the orientation of the radiation source, the X-ray can penetrate through area as low as beneath the chassis of the container-carried vehicle and part of the vehicle tyres, so that the inspection apparatus can perform a much broader scanning cross section.

Further, the inspection apparatus according to the present invention is simple in structure, and no special requirement is for the vehicle chassis. That is to say, a common chassis can meet the requirements of the inspection apparatus according to the present invention, so the vehicle for carrying the inspection apparatus can run as well as a common vehicle. Therefore, much components of the vehicle for carrying the inspection apparatus can be same as those of the common vehicle.

Further, the inspection apparatus according to the present invention has an excellent radiation protection means to perform perfect radiation protection.

As stated above, compared with the prior art, the mobile container inspection apparatus according to the present invention takes advantages of less working area, good radiation protection, convenient usage, broad inspection cross-section, and clear radiographic image. Even if in an adverse situation, the apparatus can work normally if required.

BRIEF DESCRIPTION OF THE ACCOMPANYING DRAWINGS

THE BEST MODE FOR CARRYING OUT THE INVENTION

The invention will be described in detail by reference to the accompanying drawings and the specific embodiments.

Figure 1A:
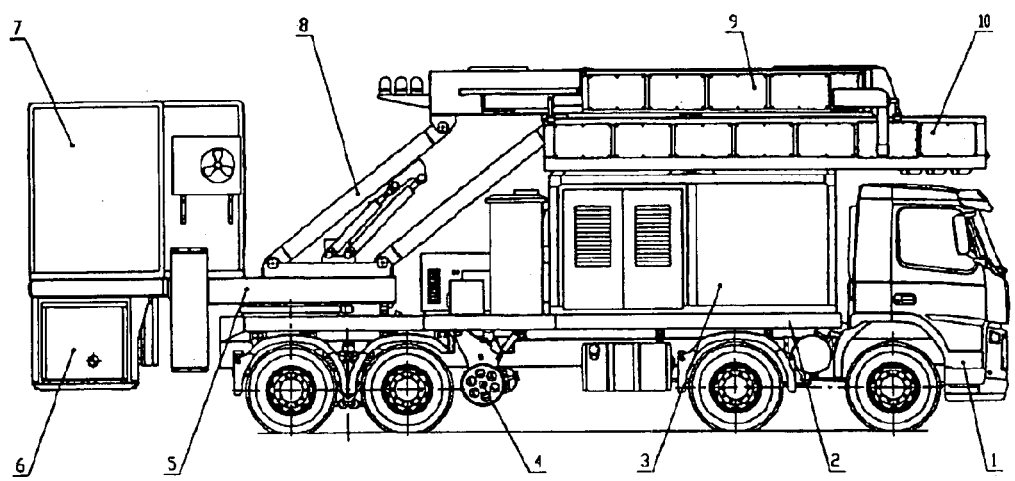
FIG. 1A is a view of the scanning vehicle of the mobile container inspection apparatus according to the present invention.
Figure 1B:
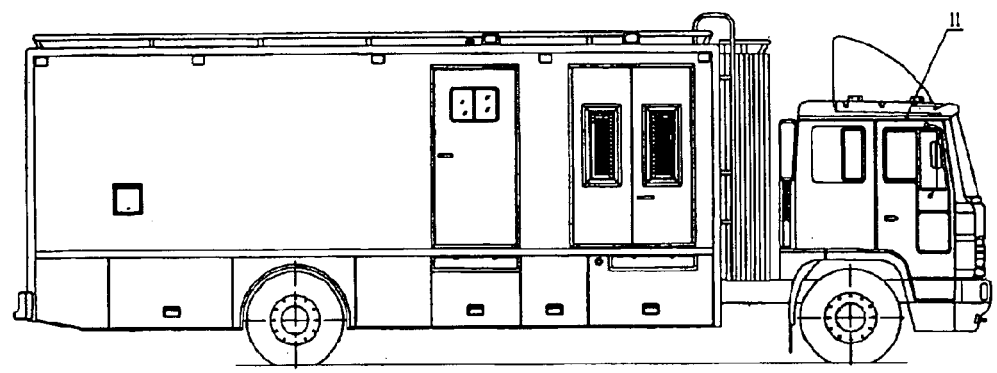
FIG. 1B is a view of the control vehicle of the mobile container inspection apparatus according to the present invention.
Figure 2:
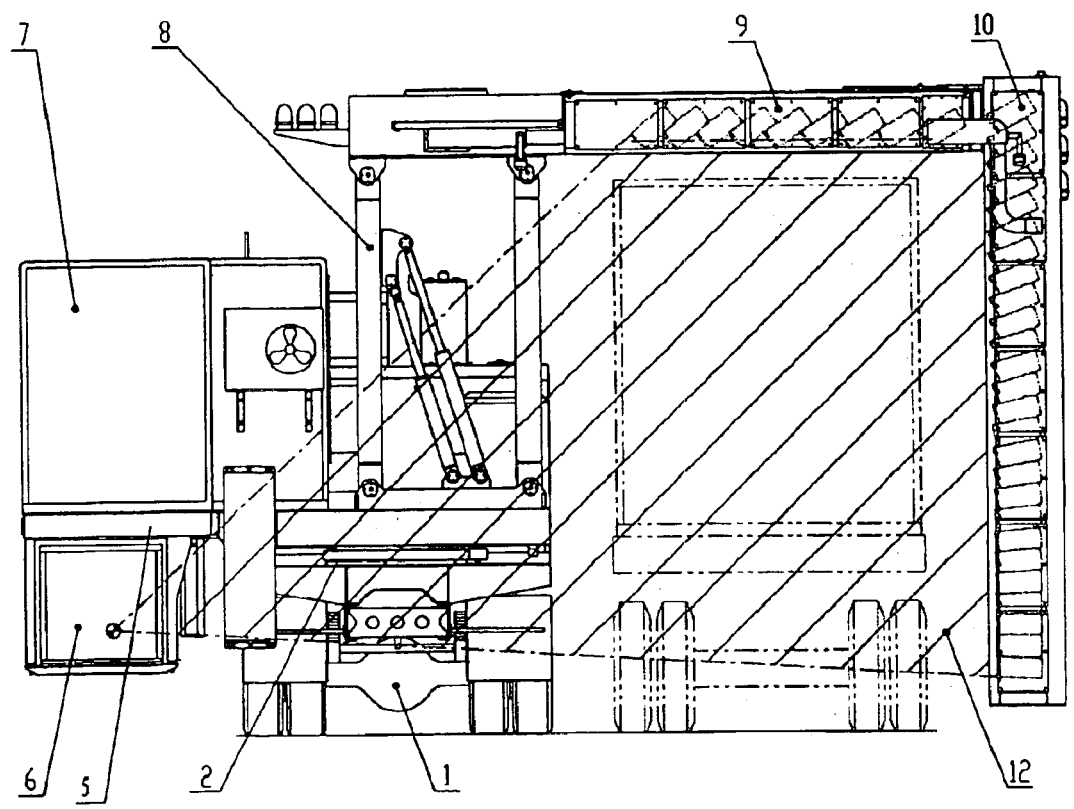
FIG. 2 is a back view of the working state of the scanning vehicle as shown in the FIG. 1.
Figure 3:
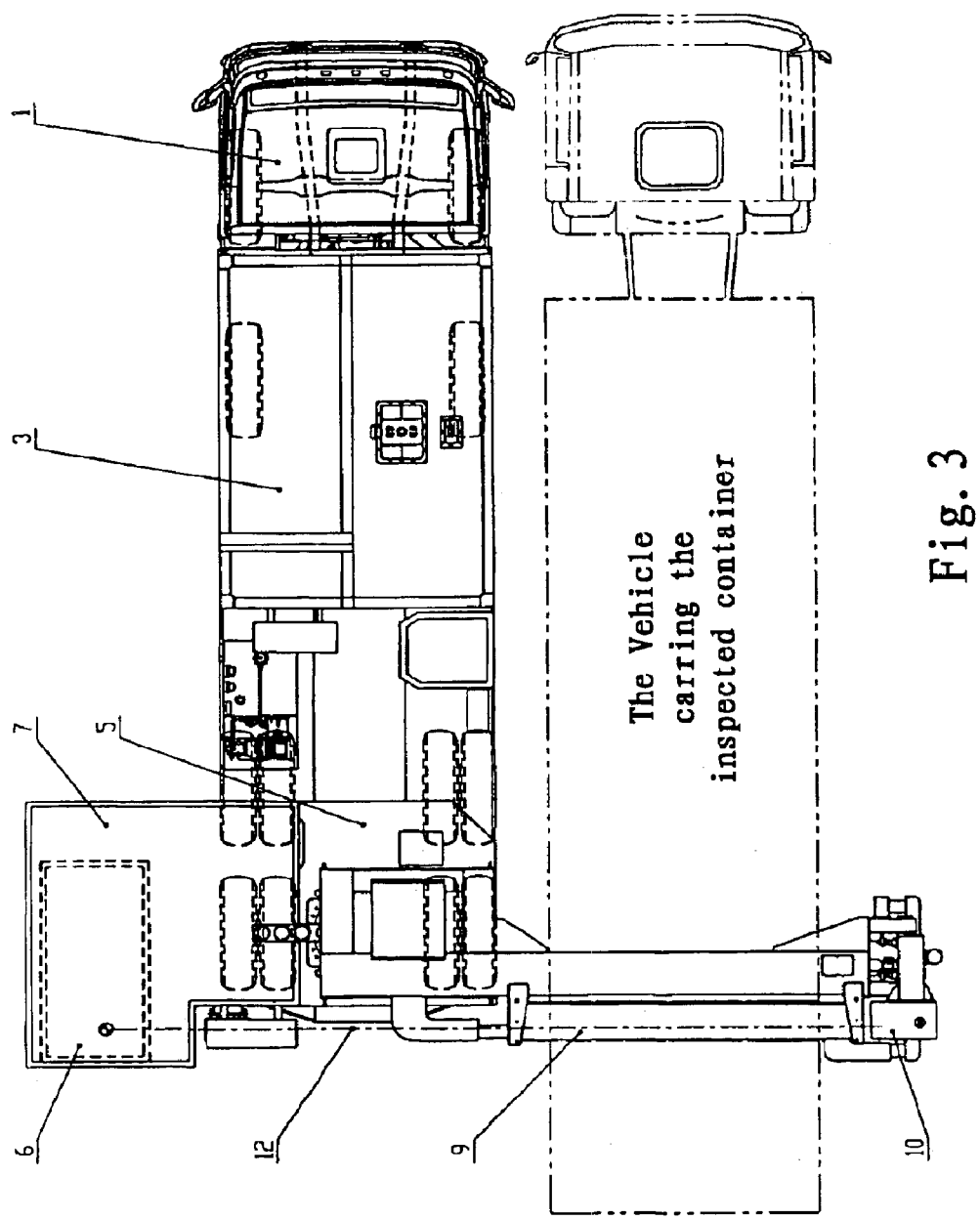
FIG. 3 is a top view of the working state of the scanning vehicle as shown in the FIG. 1.

As shown in FIGS. 1 to 3, a vehicle-carried mobile container inspection apparatus according to the present invention comprises two vehicles, one of which is the scanning vehicle 1, and the other one of which is the control vehicle 11, and the remote control units that control the two vehicles. The main body bracket of the scanning vehicle 1 is a general chassis 2, in the front of which is provided with the first box-shaped cabin 3. In the first box-shaped cabin 3, there are provided with a radio transmitter, a diesel generator with its control units, and a workroom protected by a X-ray radiation protection material. In the working room, there is provided with a scanning control module, and an operation/inspection module. In the rear portion of the chassis 2, there is provided with a relatively rotatable platform 5. A parallelogrammical bracket 8 which is hinged together by means of four linkage bars is mounted on the rotatable platform 5. The upper horizontal linkage bar of the parallelogrammical bracket 8 extends to form a horizontal arm or the first arm 9 containing some detectors. Another end of the first arm 9 is linked to a second arm 10 which is provided with detectors, oriented in its vertical gesture when the second arm 10 is in its working state, and drawn back to its horizontal gesture when the scanning vehicle 1 is or is going to be in transportation state. A hydraulic cylinder which is capable to stretch out and draw back is provided between the arms 9 and 10 so as to make the second arm 10 perpendicular or parallel to the horizontal arm or the first arm 9. On the rear part of the rotatable platform 5, there is provided with the second box-shaped cabin 7 and the third box-shaped cabin 6. The second box-shaped cabin 7 is located on the top of the third box-shaped cabin 6. The control unit of a radiation source is accommodated in the second box-shaped cabin 7. The third box-shaped cabin 6 within which a radiation source is accommodated is arranged under the rotatable platform 5, so that the X-ray radiation source is located beneath the general chassis 2, and is capable to keep facing the hanging down second arm 10 and the first arm 9. A driving means 4 is mounted near a rear wheel of the scanning vehicle 1 to smoothly move the scanning vehicle 1 forward or backward. The driving means 4 is comprised of a reducer, a driving hydraulic cylinder, a friction driving wheel and a bracket, wherein the reducer and the friction driving wheel linked with each other are mounted under general chassis 2. One end of the driving hydraulic cylinder is hinged with the middle part of the bracket, and the other end of the driving hydraulic cylinder and the upper part of the bracket are mounted separately on the general chassis 2. A radio transmitter, an image acquisition module, an operation/inspection module, and a diesel generator with its control units are accommodated in the control vehicle 11.

When inspecting a container, the rotatable platform 5 mounted on the scanning vehicle 1 turns 90 degrees. Then, the parallelogrammical bracket 8, the first arm 9 and the second arm 10 forms a portal-shaped frame. A control signal can be sent out from a radio transmitter on the control vehicle 11 and received by a radio receiver on the scanning vehicle 1, or the scanning control module on the scanning vehicle 1 is used so as to make the portal-shaped frame straddling the container to move along the container for inspecting the container. The radiation source from which a fan-shaped X-ray beam 12 emit is located after the rear part of the general chassis 2, and the lowest beam beneath the chassis 2 penetrates through the container carrying vehicle. The radiation beam penetrating through the container being inspected is detected by the detectors mounted in the horizontal or first arm 9 and the vertical or second arm 10, so as to produce the corresponding radiographic signals and send thereof to image acquisition module, so that the image signals are transmitted by the image acquisition module to the control vehicle 11 or the operation/inspection module on the scanning vehicle 1. As a result, the scanning results are displayed on a computer screen.

To operate the device according to the present invention, a remote control unit mounted on the control vehicle 11 can be employed to control all the operation of the scanning vehicle 1. By means of the remote control module, the wheels are driven to move the scanning vehicle 1. The radiation source sends out X-rays to automatically scan the container staying in the scan channel for inspecting the container, so as to output the obtained electrical signals. Then the radiographic image of the container being inspected is obtained by means of the remote control unit. When it is necessary for the apparatus according to the present invention to be moved to another site to perform inspection of containers, it is feasible to start up the hydraulic system of every hydraulic cylinders and change the scanning vehicle 1 from the scanning mode to its transport mode. Then the scanning vehicle 1 is suitable to run on the normal road. When it is not suitable to use the two-vehicle mode in some emergency cases, the inspection for a container could be performed with a singe-vehicle mode, i.e. only using the scanning vehicle 1. However, unnecessary details of some procedures for inspecting a container, which are the same as those of the prior art, are not given here.

It will be appreciated that, the radiation source used in the present invention can also be an electron linear accelerator, a X-ray machine, or other radioisotopes such as the y source. In addition, the power to change the scanning vehicle from its transport mode to its scanning mode will be equivalent with some other ways, such as the gas-dynamic or electron-dynamic system instead of the hydraulic system. All such variations and modifications are intended to be within the scope of protection of the present invention.

What is claimed is:

1. A vehicle-carried mobile container inspection apparatus comprising a rotatable platform (5) arranged in a rear portion of a chassis (2) of a scanning vehicle (1), a parallelogrammical bracket (8) arranged on the rotatable platform (5), formed by four linkage bars hinged one to another and driven by an uprighting means, a first arm (9) extended from the upper horizontal bar of the parallelogrammical bracket (8) and provided with detectors, and a second arm (10), the upper end of which is associated with the first arm (9) at the end of the first arm (9) opposite to the parallelogrammical bracket (8), wherein the second arm (10) is also provided with detectors, characterized in that the mobile container inspection apparatus further comprises a first box-shaped cabin (3) arranged in the front portion of the chassis (2) and provided with a workroom accommodating a scan control module, an image acquisition module and an operation/inspection module; and a second box-shaped cabin (7) and a third box-shaped cabin (6) both arranged on the rear portion of the rotatable platform (5), in which the second box-shaped cabin (7) is arranged on the top of the third box-shaped cabin (6), a control unit of a radiation source is accommodated in the second box-shaped cabin (7), the third box-shaped cabin (6) is arranged under the rotatable platform (5), the radiation source is arranged in the third box-shaped cabin (6), the level of the radiation source from which an X-ray beam is emitted is arranged below the level of the chassis (2), the scanning vehicle (1) is provided with a driving means (4) to smoothly move the scanning vehicle;

the rotation inducing platform (5) is provided with a rotatably driving means, when inspecting a container, the rotatable platform (5) is driven to turn 90 degrees, and the second arm (10) turns into its vertical gesture, so that a portal-shaped frame is formed by means of the parallelogrammical bracket (8), the first arm (9) and the second arm (10), a fan-shaped X-ray section (12) is formed after the rear end of the chassis (2) and in the plane where the first arm (9) and the second arm (10) are in operation.

2. A vehicle-carried mobile container inspection apparatus as claimed in the claim 1, characterized in that the first box-shaped cabin (3) is further provided with a diesel generator with its control units.

3. A vehicle-carried mobile container inspection apparatus as claimed in the claims 1 or 2, characterized in that the apparatus further comprises a control vehicle (11) accommodating an image acquisition module, an operation/inspection module, and a diesel generator with its control unit.

4. A vehicle-carried mobile container inspection apparatus as claimed in the claims 1 or 2, characterized in that the chassis (2) is the same as that used in a common vehicle.

\* \* \* \* \*